(12) United States Patent
Mulhauser et al.

(10) Patent No.: US 7,748,980 B2
(45) Date of Patent: Jul. 6, 2010

(54) DISPENSER FOR DENTAL COMPOSITIONS

(75) Inventors: Paul Mulhauser, New York, NY (US); Karl D. Kirk, III, New York, NY (US); David Czarnecki, New Hyde Park, NY (US); Richard Nagel, West Chicago, IL (US)

(73) Assignee: Bisco, Inc., Schaumburg, IL (US)

( * ) Notice: Subject to any disclaimer, the term of this patent is extended or adjusted under 35 U.S.C. 154(b) by 16 days.

(21) Appl. No.: 11/522,825

(22) Filed: Sep. 14, 2006

(65) Prior Publication Data

US 2008/0070187 A1    Mar. 20, 2008

(51) Int. Cl.
*A61M 5/00* (2006.01)
*B67D 7/60* (2010.01)
*B67D 7/70* (2010.01)
*A61C 5/04* (2006.01)
*B65D 88/54* (2006.01)

(52) U.S. Cl. .................. 433/89; 604/208; 604/191; 222/137; 222/326; 222/327; 222/391

(58) Field of Classification Search ............. 433/80–84, 433/87–90; 222/137, 326, 327, 391, 287; 604/208, 209, 191
See application file for complete search history.

(56) References Cited

U.S. PATENT DOCUMENTS

| | | | | |
|---|---|---|---|---|
| 3,827,602 A | * | 8/1974 | Nicholls | 222/137 |
| 4,591,072 A | * | 5/1986 | Oshikubo | 222/44 |
| 4,693,684 A | * | 9/1987 | Blatherwick et al. | 433/90 |
| 4,936,833 A | * | 6/1990 | Sams | 604/232 |
| 5,735,437 A | * | 4/1998 | Broyles et al. | 222/137 |
| 5,747,709 A | * | 5/1998 | Oshikubo | 73/864.18 |
| 6,007,515 A | * | 12/1999 | Epstein et al. | 604/82 |

\* cited by examiner

*Primary Examiner*—Cris L Rodriguez
*Assistant Examiner*—Yogesh Patel
(74) *Attorney, Agent, or Firm*—Homer W. Faucett, III; Ice Miller LLP (57) ABSTRACT

The present invention relates to an apparatus for providing specifically metered doses of at least two flowable dental materials in desired ratios to one another. In particular, the present invention allows for controlled metering and dispensing of two or more flowable dental substances which when subsequently mixed form a dental bonding composition, dental adhesive, dental cement, or other dental restorative or preparative materials. Specifically, one embodiment of the present invention utilizes a multi-rack system as well as a drive spring action to provide a substantial mechanical advantage to the user such that a relatively long throw of the dispensing button creates a relatively short, metered distance of movement of the multiple racks and corresponding pistons in the each lumen of a cartridge containing the component of the desired dental composition, allowing for small, metered doses of each flowable dental component to be dispensed from the apparatus in the proper proportions.

24 Claims, 12 Drawing Sheets

DISPENSER FOR DENTAL COMPOSITIONS

BACKGROUND

Useful dental compositions include compositions resulting from the admixture of two or more components. For example, self-curing and/or self-priming dental adhesives and cements often comprise two or more components, one of which initiates the curing or hardening process when brought into contact with the other component(s). Some dental compositions are also presented in multi-component form to minimize or avoid long-term storage stability concerns otherwise present if all the components were present and in contact with one another in a single container. Such components of such multi-component dental compositions are also preferably combined with one another in certain ranges or ratios to one another to yield optimal results. Examples of multi-part dental compositions include dental bonding adhesives such as those represented by U.S. Pat. No. 5,348,988 to Suh et. al, and other dental adhesive and cement compositions well-known in the art. Multi-component dental restorative systems that include a colorant in one or more of its components may also require a separation of such components until admixing in metered amounts, depending on the nature of the colorant(s) and reactivity with the other compounds and/or the curing system employed in the restorative system.

In practice, such multi-part dental compositions are mixed immediately prior to their use in order to prevent biological or chemical contamination and to preclude the mixed composition from curing or degrading before it is applied to the target surface. However, mixing of these dental compositions is often done in small quantities, and should ideally be metered with great precision to ensure that the mixed composition contains the proper proportion of the multiple components. Mixing the small volumes of these materials called for in dental restorations at the proper ratio is difficult in a clinical setting. In many cases, these dental compositions are mixed while the practitioner or technician is manipulating the target surface, or while the dental technician is at least partially occupied with attending to a patient. Metering small volumes of these two or more component systems while manipulating the restoration site in a patient's mouth can be difficult, particularly in light of the time constraints established by the curing of the materials used. Therefore, a system for providing metered doses of a plurality of flowable dental materials in desired small volumes and at specific ratios in a system easily manipulated by the dental practitioner would be greatly appreciated in the art.

Previous attempts have been made to provide metered dosage of two-part adhesive systems, such as dual lumen syringes and similar devices. However, the expense of multi-component dental compositions, as well as the small range for error that is required to achieve the ideal mixture of the multiple components renders many of these previous systems unwieldy and impractical in laboratory and clinical dental settings. For example, a two lumen syringe might meter two components in appropriate proportions if the plunger is pushed squarely, but if the user pushes with greater force on either side of the plunger, the proportion of the components will likely vary. Further, such systems do not meter out the total volume of the combined components, which can lead to waste or improper proportion if the combined components must be further mixed with another component in a particular proportion. Typically, such prior art systems are single use dispensers, requiring the clinician to discard the entire system once the contents of one or more lumen are exhausted, and require the purchase of an entirely new system to replace or vary the applied dental composition. Therefore, a dispenser that readily meters out a prescribed total volume of components in a consistent proportion would be greatly appreciated, particularly if such a system comprises a replaceable cartridge or refillable lumens.

BRIEF DESCRIPTION OF THE DRAWINGS

FIGS. 6c and 6d show a side plan view of the operation of the mechanical system of a dispenser according to one aspect of the present invention.

DESCRIPTION

According to one aspect of the present invention, a reusable hand-held dispenser 5 as shown in FIGS. 1a and 1b, 2, 3a-3c 4 and 4a comprises a body 10, inner mechanical systems 20, and replaceable cartridges 30 which may be engaged for dispensing fluids therein. In addition, dispenser 5 may comprise a dispensing button 40, a cartridge eject button 50, and a cap 60.

Figures 1A, 1B:
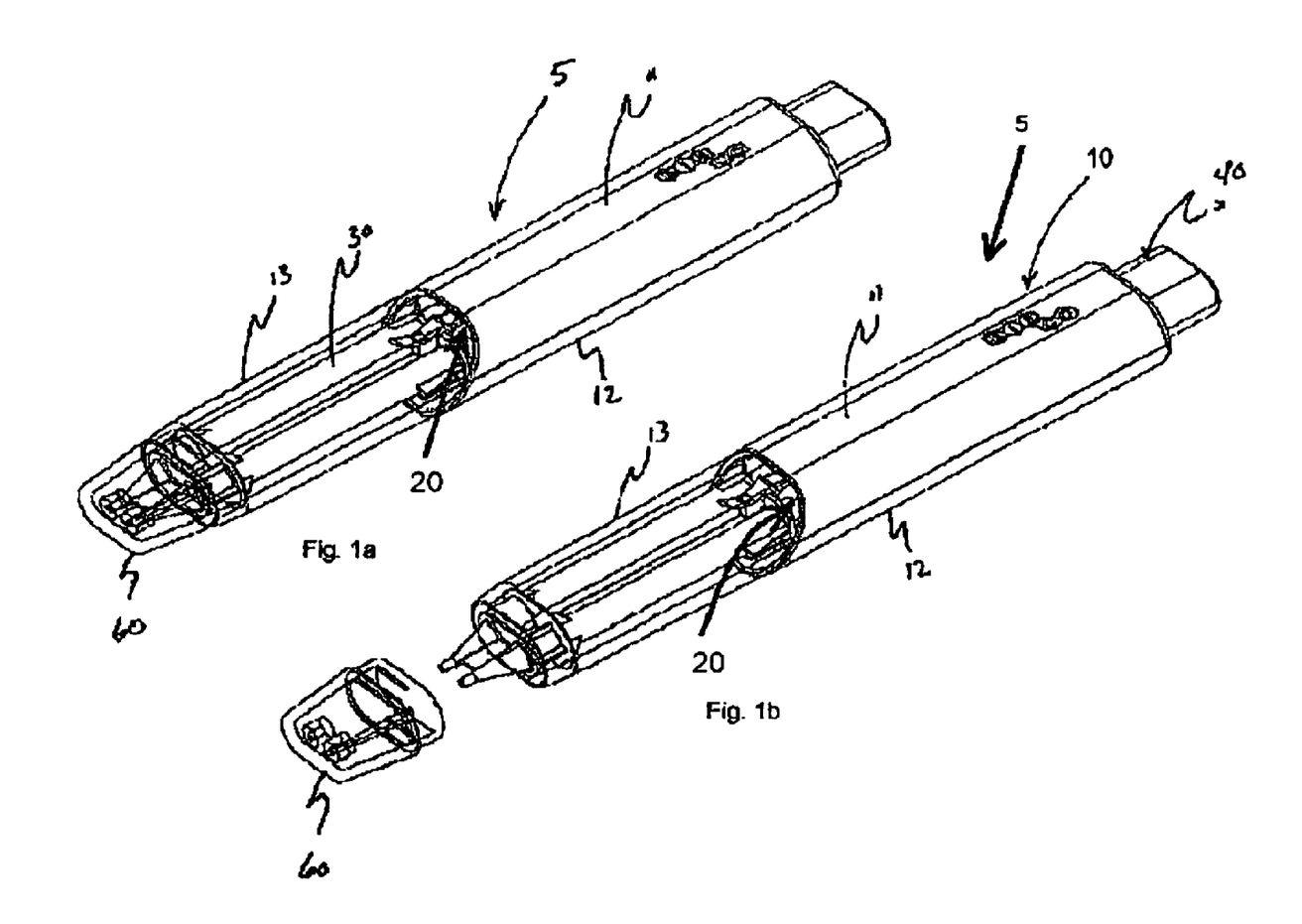
FIG. 1a is a top perspective view of a dental composition dispenser according to one embodiment of the present invention.
FIG. 1b is a top perspective view of a dental composition dispenser with the cap removed according to one embodiment of the present invention.
Figure 2:
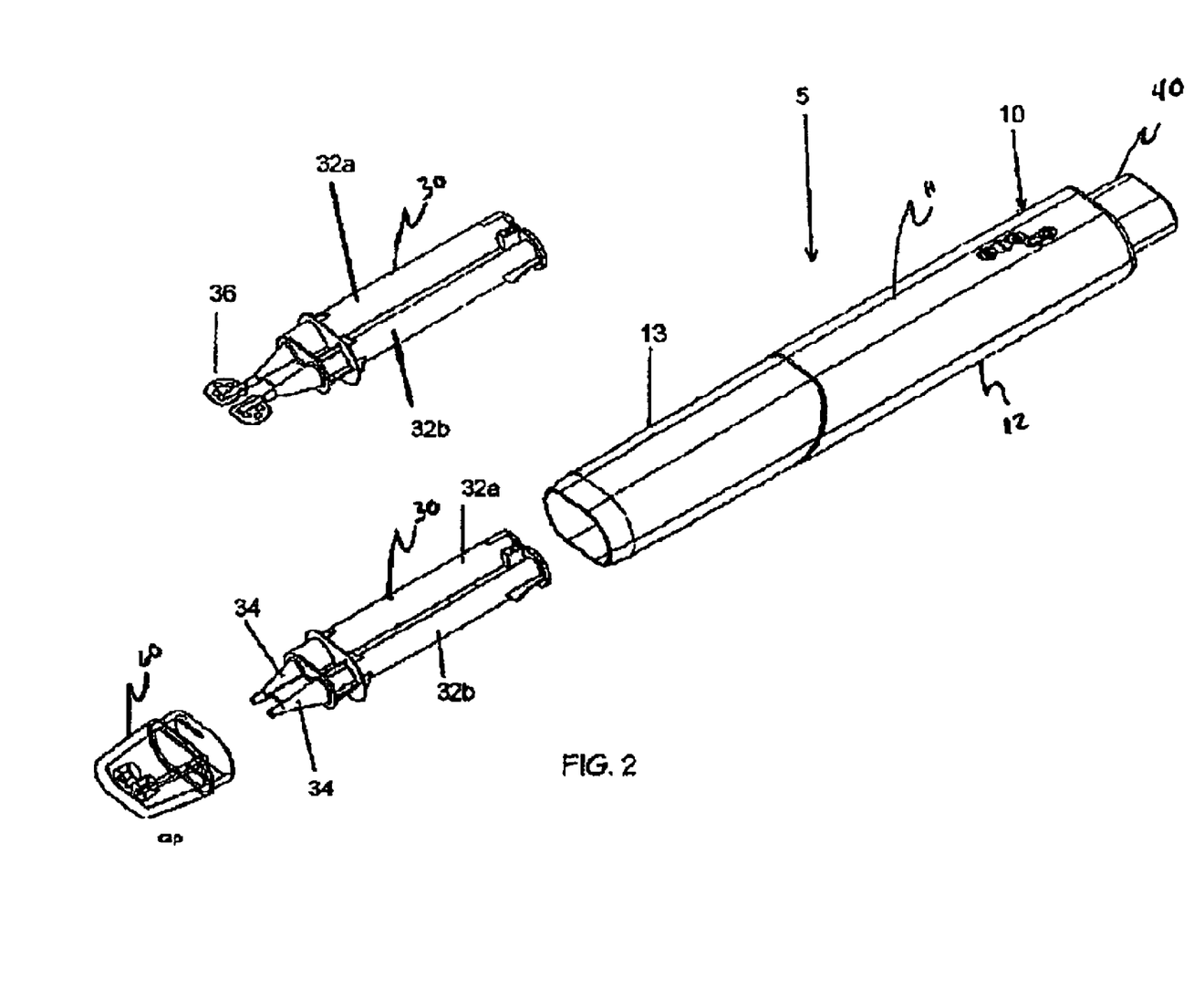
FIG. 2 is an exploded perspective view of a dental composition dispenser according to one embodiment of the present invention with the cap portion removed and cartridge removed from the dispenser.
Figures 3A, 3B:
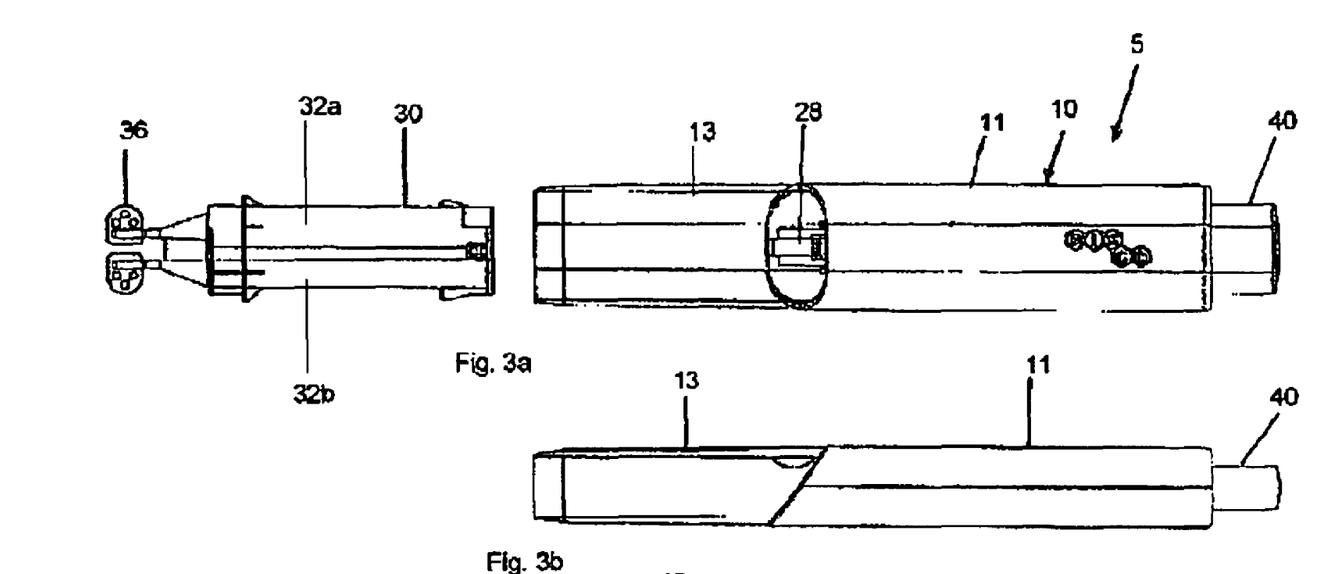
FIG. 3a is a top plan view of the dental composition dispenser of FIG. 1 according to one embodiment of the present invention.
FIG. 3b is a side plan view of the dental composition dispenser of FIG. 1 according to one embodiment of the present invention.
Figure 3C:
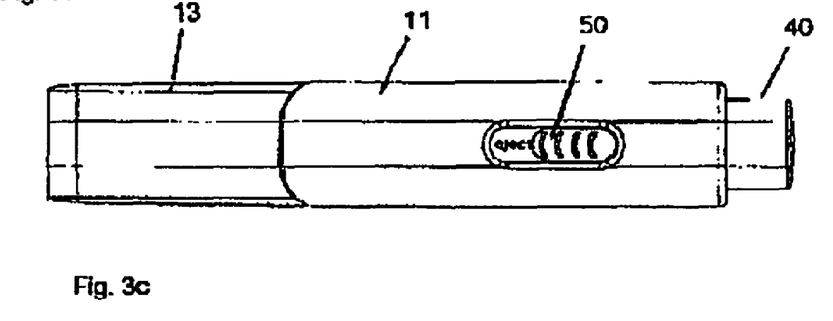
FIG. 3c is a bottom plan view of the dental composition dispenser of FIG. 1 according to one embodiment of the present invention.
Figure 4:
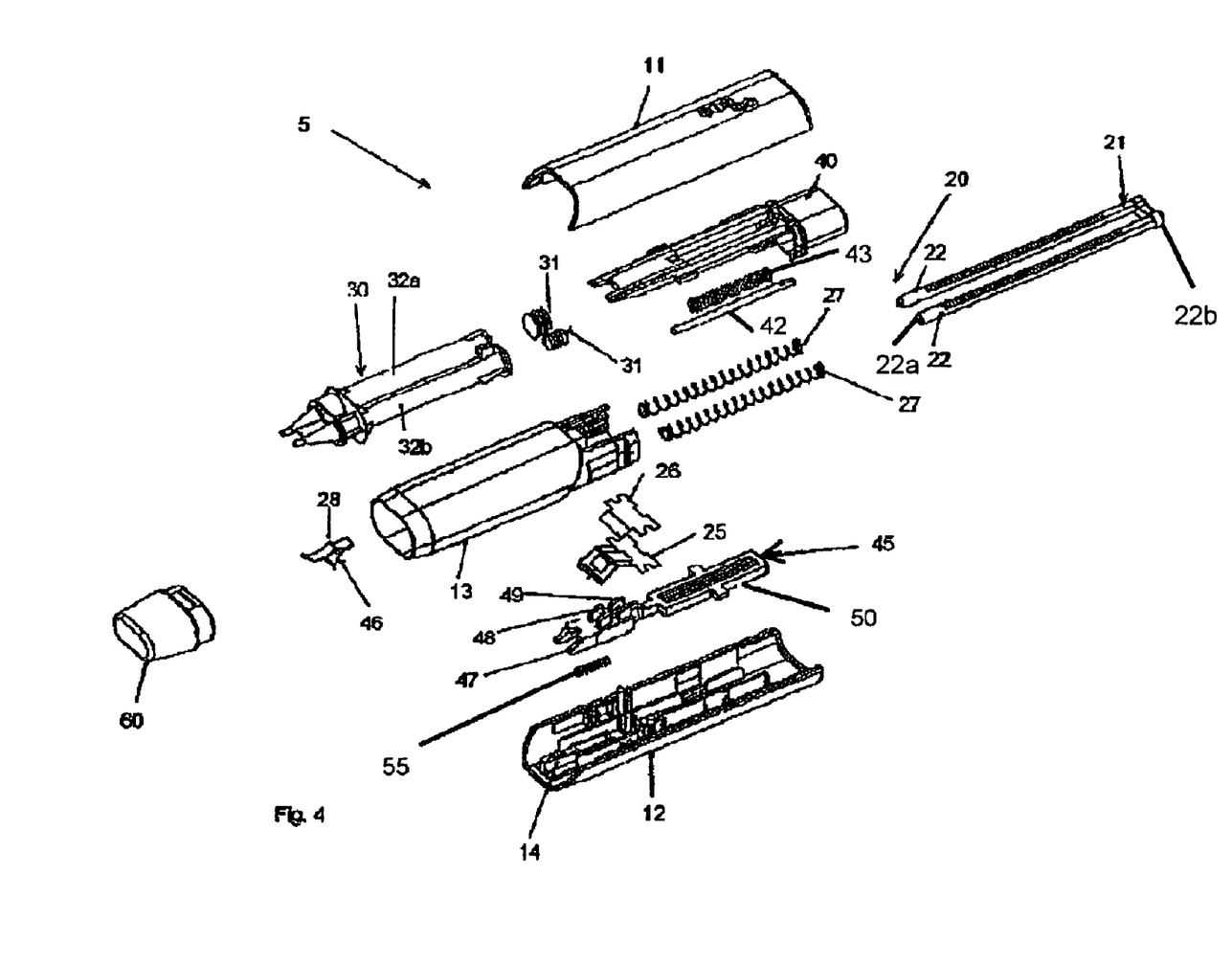
FIG. 4 is an exploded perspective view of a dental composition dispenser according to one embodiment of the present invention.

Turning now to FIGS. 1 through 3, according to one embodiment of the present invention, body 10 comprises a top shell 11, a bottom shell 12, and a chamber 13. The top shell 11 and bottom shell 12 encloses the inner mechanical systems 20 (shown in FIG. 4), and the chamber 13 receives the cartridges 30 and aligns the cartridges 30 with the inner mechanical systems 20 to allow properly metered dosing when the mechanical systems 20 is activated. As shown in FIG. 4, mechanical systems 20 comprise a rack system 21 having a plurality of racks 22, the racks 22 having teeth 23 (as shown in FIGS. 6-7) registered against one another, a drive spring 25, a pawl spring 26, and rack return springs 27. According to one aspect of the present invention, either all or a portion of the non-spring components of dispenser 5 may be created from injection molded compositions well known in the art that are chemically compatible with commonly used dental disinfecting solutions and the dental materials being dispensed. Other compatible materials may be used, such as glass, metals, and hard plastics. Further, it will be appreciated that spring components may comprise conventional spring materials for rack return springs 27, ejector return spring 51, button return spring 42, and the materials for drive spring 25, pawl spring 26, cartridge ejector spring 46, and retainer spring 28 components may comprise elastic materials or metallic materials with an elastic equivalent, including but not limited to high tensile strength steel, heat treated spring steel, or 17-7 grade steel.

It will be appreciated that several embodiments of the present invention, and that the following exemplary embodiments are presented as nonlimiting. For example, turning to FIGS. 1-4a, it will be appreciated that body 10 may comprise an upper shell 11 and a lower shell 12 as disclosed above, and shown in FIG. 3, and that mechanical systems 20 are substantially enclosed therein once upper shell 11 and lower shell 12 are fastened together, either through the use of solvents, interlocking parts, fusion (such as ultrasonic fusion or welding) of the two parts, fasteners, or other means known in the art. Further, according to one embodiment, it will be appreciated that rack return springs fit over the individual racks 22 of rack system 21.

Further, according to one embodiment, button system 40 lies substantially within body 10 when assembled, such that wedge portion 41 moves in a substantially forward and backward motion within body 10 as a user depresses an exposed external portion of button system 40. The internal and external functional aspects of the button are optionally molded as one piece, but may be provided by separate parts. Button return spring 42 and button return rod 43 (see FIGS. 4 and 4a) interact with button system 40 and interior portions of body 10 such that when button system 40 is depressed, button return spring 42 is compressed. Button return rod 43 fits within button return spring 42, and button return spring 42 exerts a force upon button system 40 when button return spring 42 is compressed. Button return spring 42 biases the button rearward (away from cartridge 30) with respect to body 10. Button return rod 43 is operable to align button return spring 42, but it will be appreciated that other means for aligning button return spring may be used. Further, in one embodiment, drive spring 25 and pawl spring 26 (see FIG. 4a) are anchored to an interior portion of body 10, optionally on the interior of lower shell 12. In one embodiment, pressure pad 29 (see FIG. 4a) may be positioned in lower shell 12 at a position that will cause pressure pad 29 to engage rack return springs 27 and prevent rack return springs from interfering with drive spring 25 and pawl spring 26.

Figure 4A:
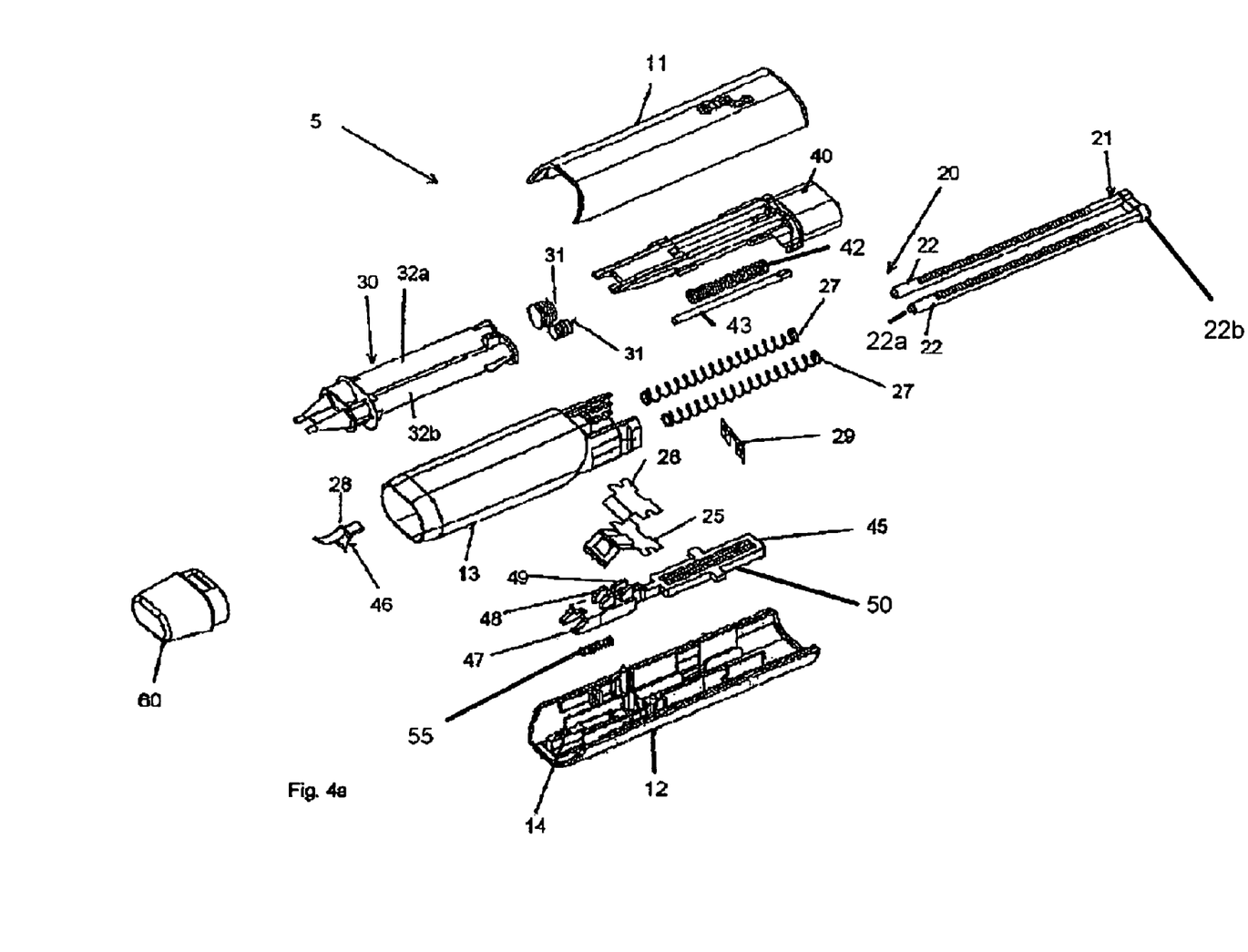
FIG. 4a is an exploded perspective view of a dental composition dispenser according to one embodiment of the present invention.
Figures 5A, 5B:
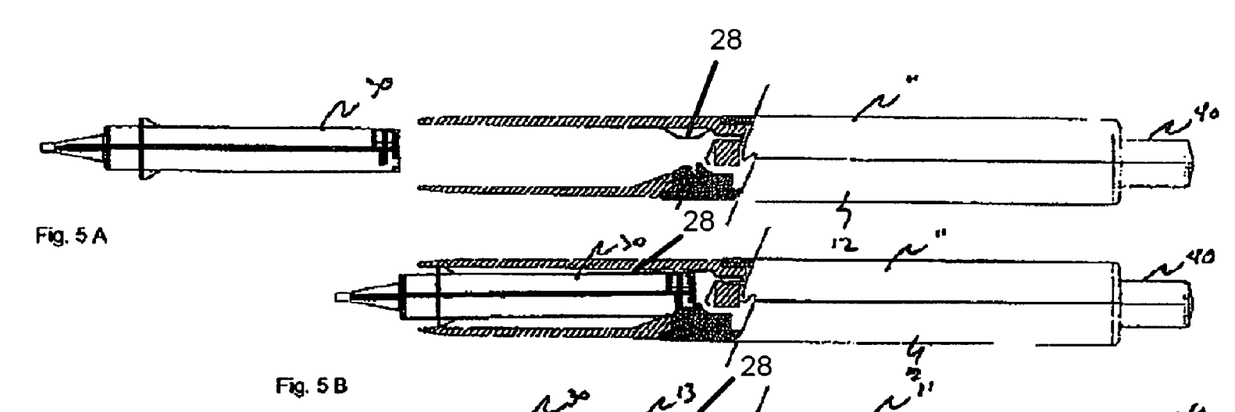
FIG. 5a is a side plan view of the chamber of a dental composition dispenser and cartridge with the cartridge removed according to one embodiment of the present invention.
FIG. 5b is a side plan view of the chamber of a dental composition dispenser with a cartridge partially inserted, according to one embodiment of the present invention.
Figures 5C, 5D:
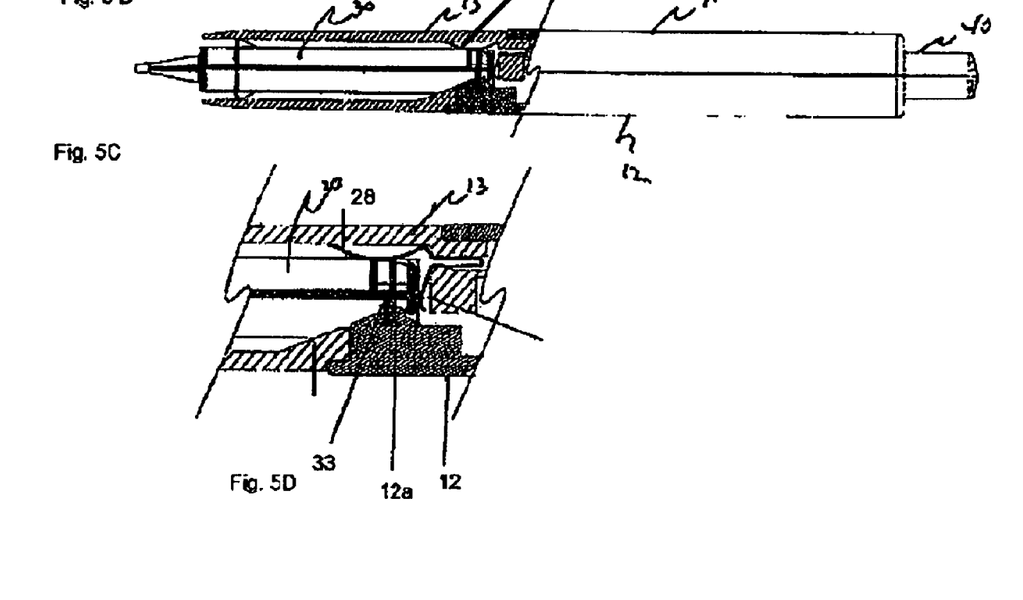
FIG. 5c is a side plan view of the chamber of a dental composition dispenser with a cartridge fully inserted, according to one embodiment of the present invention.
FIG. 5d is a partial side plan view of the chamber of a dental composition dispenser showing a close-up of the fully inserted cartridge of FIG. 5c, according to one embodiment of the present invention.

Additionally, according to one embodiment, ejector 45 is seated within lower shell 12 such that button 50 protrudes through an opening in lower shell 12 as shown in FIGS. 3c, 4 and 4a. Ejector 45 is operable to move in a forward and backward direction as further disclosed below.

It will be appreciated that the dispenser 5 will likely come in contact with various disinfectants used in the dental field, of which some may be caustic or likely to erode or oxidize certain materials. Therefore, according to certain embodiments of the present application, materials that are resistant to corrosion or breakdown by oxidative materials may be preferred. For example, stainless steel or corrosion resistant materials may be used for the spring components or other components of the dispenser, or a paint or polymer coating applied to such materials to inhibit or prevent corrosion of susceptible surfaces.

Figure 6A:
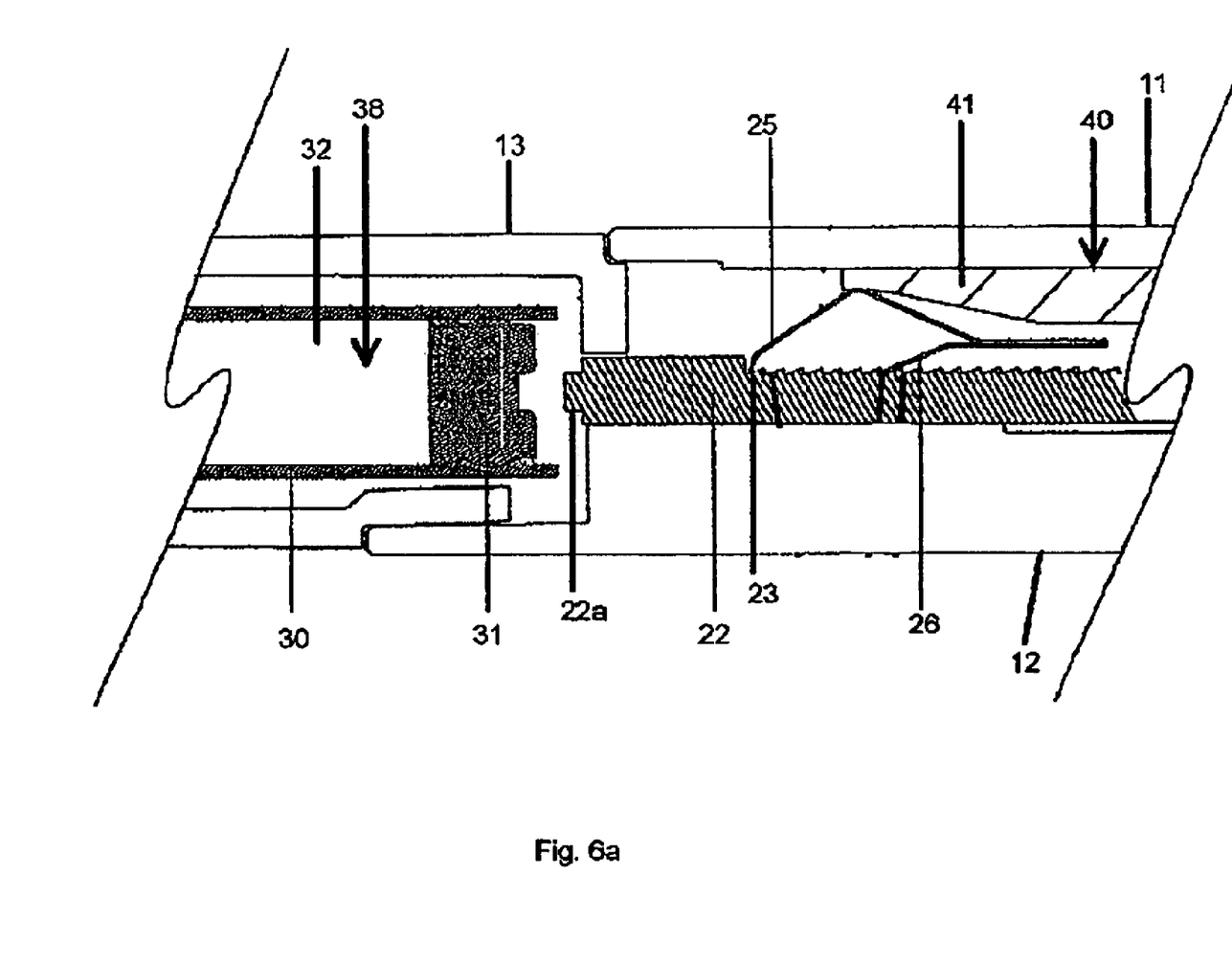
FIGS. 6a and 6b show a side plan view of the operation of an inner mechanical system of a dispenser according to one aspect of the present invention.
Figure 6B:
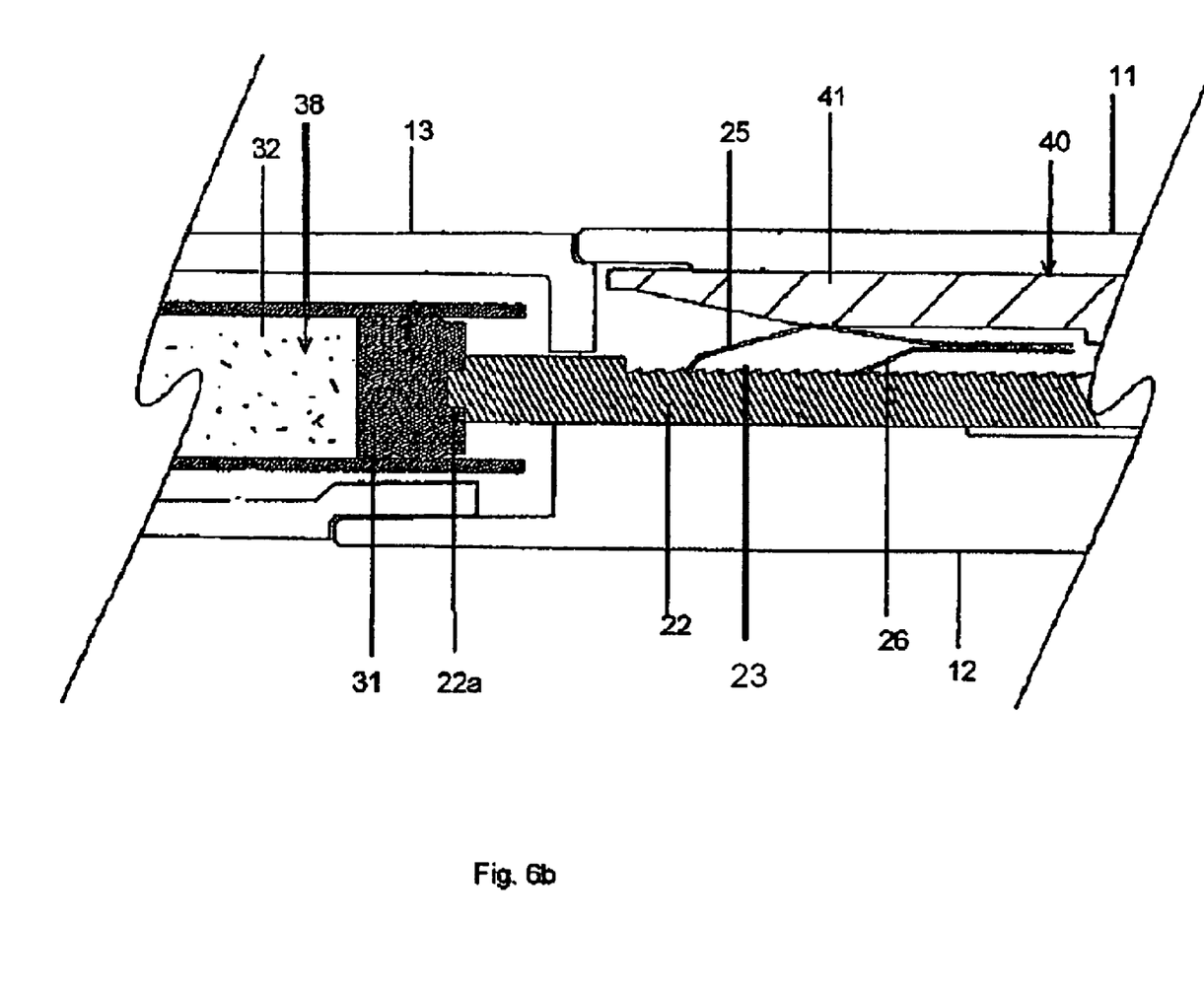
Figure 6D:
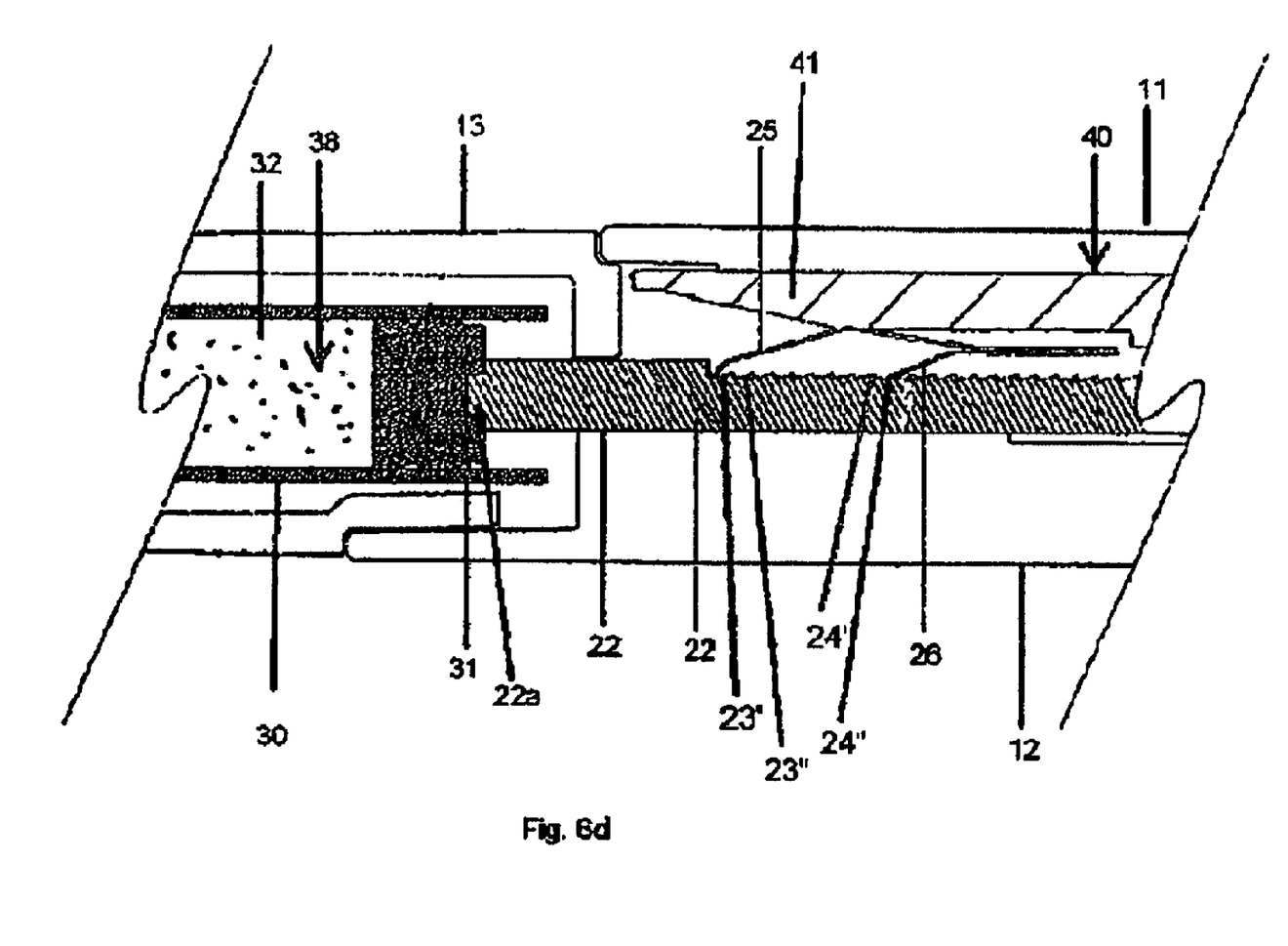
Figure 6E:
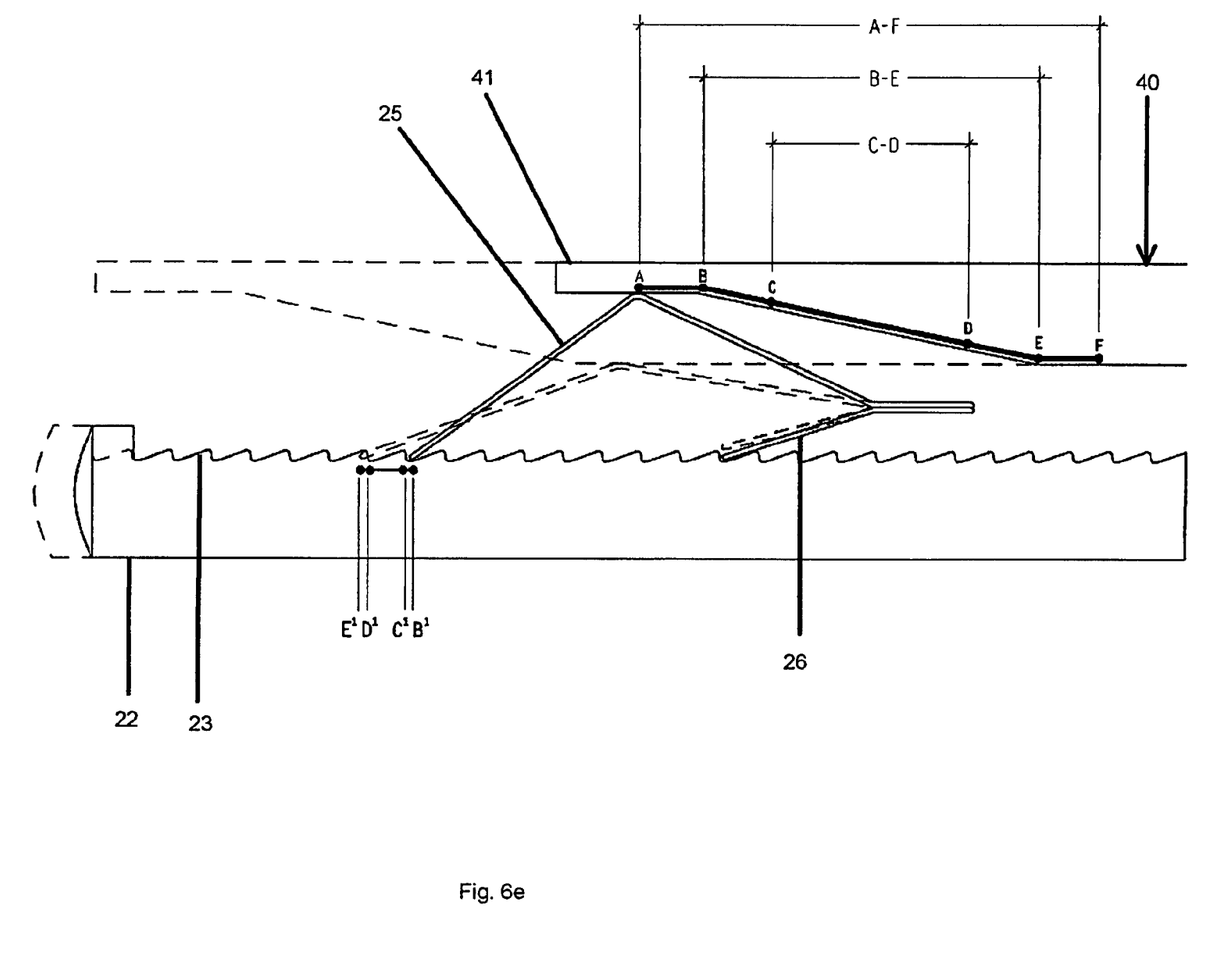
FIG. 6e is a side plan view of the operation of the mechanical system of a dispenser according to one aspect of the present invention representing action of the drive spring and pawl spring with respect to the rack system according to one embodiment of the present invention.
Figure 7:
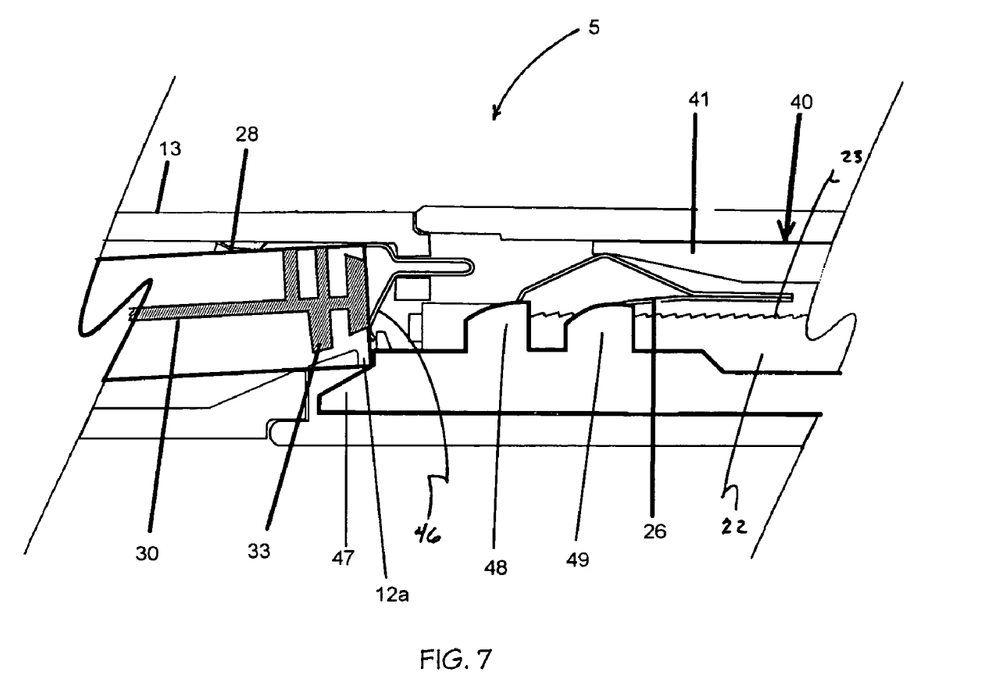
FIG. 7 is a side plan view of a chamber, a cartridge, and cartridge ejector system of a dental composition dispenser according to one embodiment of the present invention.
Figure 8C:
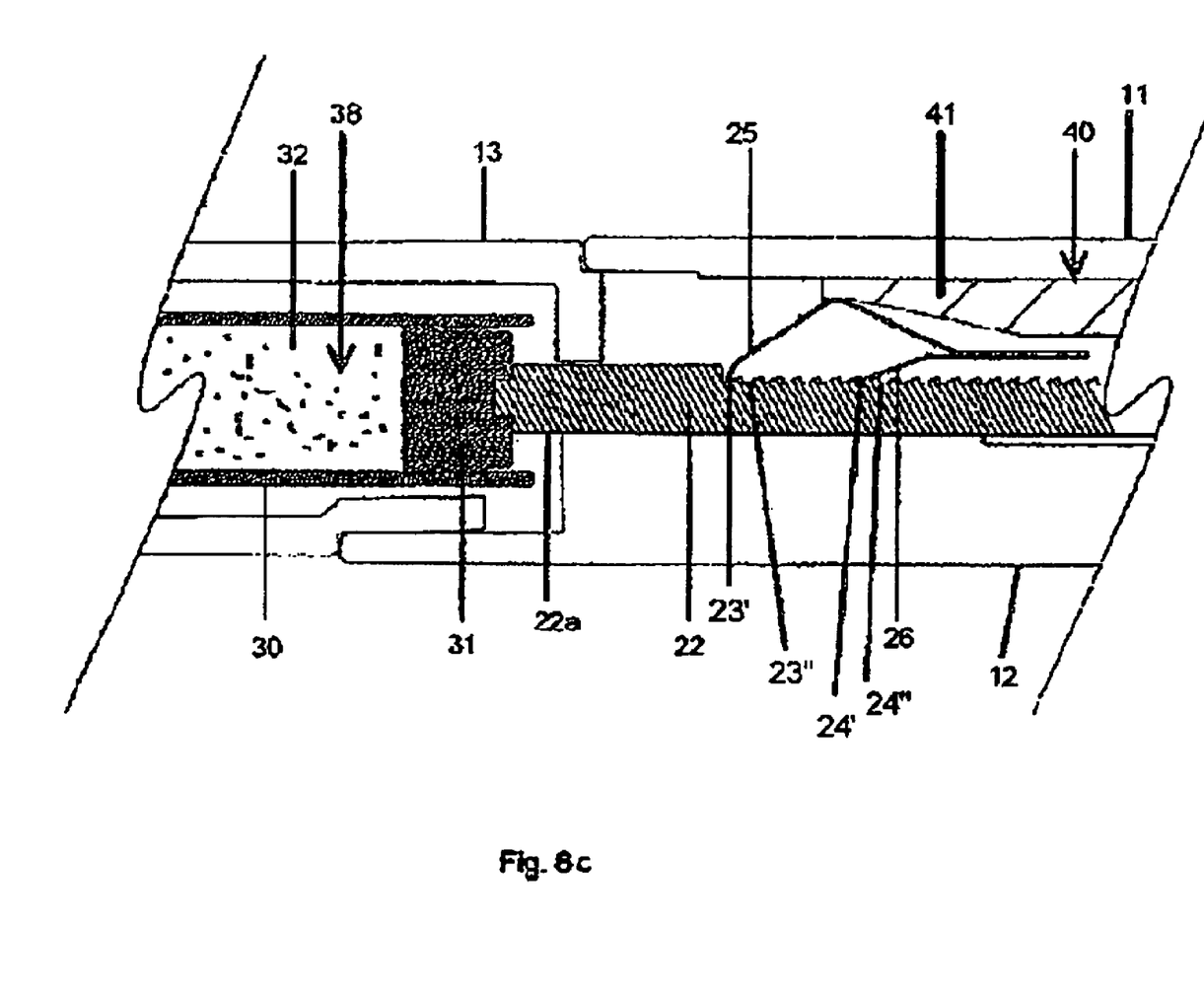

In one embodiment of the present invention, the operation of which is shown in FIGS. 4, 4a, 6c, and 6d, drive spring 25 engages a first tooth 23' on a first rack 22 and a corresponding first tooth 23' on a second rack 22, with both racks being of substantially identical tooth construction. Pawl spring 26 engages a second tooth 24' on both racks a selected distance behind the teeth 23' engaged by drive spring 25. As shown in FIGS. 6c-6d, as button 40 is depressed and drive spring 25 advances rack system 21 either one or a plurality of teeth, pawl spring 26 engages a second tooth 24" on a first rack 22 and a corresponding second tooth 24" on a second rack 22. It will be appreciated that drive spring 25 may have a curved end as shown in FIGS. 6a-6d, or may have a straight tip for interacting with teeth 23 as shown in FIG. 6e. As shown in the sequences in FIGS. 6c and 6d, and in the overlay representation in FIG. 6e, when at rest, pawl spring 26 resists the pressure from rack return springs 27, adapted to fit over each rack 22 of rack system 21 to urge rack system 21 away from cartridge 30 until activation of dispensing button system 40. Rack return spring 27 is compressed between end of rack 22b and pressure pad 29. Optionally, if pressure pad 29 is not utilized, rack return spring 27 may be compressed between end of rack system 22b and a fixed point on body 10, preferably on a portion provided on lower shell 12. When a user depresses dispensing button system 40, a wedge portion 41 of button system 40 moves toward cartridge 30 and depresses the top of drive spring 25, changing the geometry of drive spring 25 as shown in FIGS. 6c, 6d, and 6e, thereby causing the front portion of drive spring 25 to move against tooth 23', and pushing both the first and second racks 22 to advance the distance between a first tooth 23' and the next tooth 23" on the rack system 21. As racks 22 advance, end 22a of rack 22 engages and advances piston 31 into lumen 32 of cartridge 30 and causes a precise amount of component of dental composition material 38 to be dispensed out of opposite end 34 of lumen 32. Simultaneously, as the rack 22 is advanced, tooth 24' moves under pawl spring 26 such that tooth 24" is now engaged by pawl spring 26. Upon release of button 40, wedge portion 41 retreats backwards away from cartridge 30, allowing drive spring 25 to disengage from tooth 23', and consequently to engage tooth 23" and further allowing drive spring 25 and pawl spring 26 to reassume their respective geometries shown in FIG. 6c, but with their respective ends now engaging teeth 23" and 24" on rack 22. As the rack system 21 advances, pawl spring 26 constrains the rack 22 in its forward achieved position and holds the rack 22 in position to be reengaged upon the next depression of button system 40. In this manner, pawl spring 26 in conjunction with rack return spring 27 further serve as an anti-hysteresis device, as rack return springs 27 cause pawl spring 26 to be in constant contact with the tooth such that rack system 21 cannot move backward when pawl spring 26 is engaged.

As can be seen in FIG. 6e, the distance traveled by the wedge portion 41 of button system 40 (A to F) is substantially farther than that traveled by the rack system 21 (B' to E'), allowing the user to depress the button 40 a reasonable distance while only causing the pistons 31 to travel a metered distance. In one embodiment, the movement of wedge portion 41 between areas C and D on the button system 41 causes the rack 22 to advance the distance between C' and D'. It will be appreciated that in the exemplary embodiment of FIG. 6e, wedge portion 41 of button system 40 includes certain flat portions that do not cause depression of drive spring 25. For example, movement of button system 40 in from reference point A to reference point B does not cause a change in geometry of drive spring 25, and therefore does not cause advancement of rack 22. However, travel of button system 40 from reference points B to E causes a change in the geometry of drive spring 25, and causes advancement of rack 22 a distance from B' to E', causing a tooth 23 to progress forward under pawl spring 26, such that pawl spring 26 is deflected upward as shown until the tooth passes under pawl spring 26.

Such a system allows rack 22 to travel a small metered distance compared to a substantially larger distance traveled by button system 40, which results in a mechanical advantage to the user. For example, this mechanical advantage may be approximately 6:1, with the user depressing the button 40 six times as far as the rack 22 will travel in response. By way of nonlimiting example, the button 40 stroke may travel a combined distance of 0.400 inches while driving rack 22 a distance of only approximately 0.045 to 0.066 inches, thereby allowing a relatively small, precisely metered, total volume of each component of the dental composition to be dispensed. By way of nonlimiting example, depression of button 40 could cause advancement of the rack 22 a distance of a plurality of teeth with each depression by changing the geometry of drive spring 25 to adjust the metered amount of dental composition to be dispensed, or such dispensed amount could be metered by changing the distance between teeth 23, or by a combination of those methods. Thus, mechanical system 20 may be modified to create a multitude of different mechanical advantages and distances traveled and the dispensed amount of the dental composition for each depression of the button system 40. Further, it will be appreciated that, rather than utilizing a flexible pawl spring 26 that deflects upward as rack 22 is advanced, a fixed notch or pawl may be utilized, and the rack 22 may move downward as a tooth 23 progresses across the fixed notch or pawl, only to have the rack 22 move back up once the apex of tooth 23 has passed under fixed notch or pawl.

According to yet another embodiment of the present application, FIGS. 6a-6b demonstrates an optional feature for ensuring that the end of rack 22a engages piston 31 upon the first depression of button system 40. Optionally, end of rack 22a may be sized and shaped in many variations, including stepped, chamfered, substantially flat, curved, or other shapes adapted to engage pistons 31 in a manner that maintains racks 22 in a substantially central alignment with respect to pistons 31. Specifically, rack system 21 is optionally sized such that upon the first depression of button system 40 after insertion of new cartridge 30 into chamber 13, the back of rack system 22 is engaged by button system 40, causing rack system 22 to advance a substantial distance, and ensuring that each front end of each rack 22 engages each piston 31. It will be appreciated that this initial advance will likely result in some of the components of dental composition 28 to be ejected from the front of cartridge 30, and such first advance ensures that each additional depression of button system 40 (as described in the previous paragraphs) results in a dispensing of a metered amount of the components of dental composition 28.

Referring now to FIG. 4a, according to one embodiment of the present application, the inner mechanical systems 20 further comprises a pressure pad 29, which interfaces with chamber 13, and which contains at least one opening to allow racks 22 to pass through pressure pad 29 while preventing rack return springs 27 from passing through the at least one opening of pressure pad 29. Pressure pad 29 is preferably located in the rear portion of bottom shell 12 in such a manner that rack return spring 27 does not interfere with the operation of drive spring 25 or pawl spring 26. Therefore, when button system 40 is depressed, rack return springs 27 oppose the forward movement of the rack system 21 due to rack return springs 27 pressing against both rack return pad 29 on one end, and rack system 21 on the other end.

As discussed above, as rack system 21 advances toward cartridge 30, the rack system 21 advances the pistons 31 within the lumens 32 of cartridge 30, thereby displacing the components of dental material 38 out of ends 34 (see FIG. 2). The lumens 32 of cartridge 30 may be sized to determine the amount of fluid displaced from each chamber of cartridge 30, thereby regulating the ratio of a first fluid to a second fluid. Since the mechanical systems 20 provide for a substantially identical travel by the plurality of racks 22, the ratio of the first fluid to the second fluid dispensed is determined by the lumen size of each chamber in the cartridge 30. As shown in FIG. 3a, a first lumen 32a may be of a greater diameter of the second lumen 32b, allowing for a ratio of metered fluid to be 3:1, or the lumens may be identical, allowing for a 1:1 dispensing, or varied according to the desired dispensing ratios of the dental compositions. A number of different ratios of the cross section area of the lumens may be created, allowing for varying dispensing ratios. Since each of the plurality of racks is advanced in identical travel distance, the ratio of the volume of a first fluid to a second fluid is a function of the cross section area of the lumen.

It will be appreciated that according to one embodiment of the present application, the total metered volume of the dental composition is a function of the distance from a first tooth on a rack to a second tooth on a rack. Because depression of button system 40 causes wedge portion 41 to engage drive spring 25 to advance rack system from a first tooth to a second tooth, the volume of each component of the dental composition dispensed per depression of the button system 40 is equal to the surface area of the cross section of the lumen multiplied by the distance from the first tooth to the second tooth. Therefore, the metered amount of dental composition dispensed per depression of the button system 40 is a function of the distance between each tooth. A shorter distance between a first and second tooth results in a smaller volume of dental composition dispensed. Further, cartridge lumen size and distance between teeth 23 can readily be adapted to ensure a particular volume of dental composition is dispensed, thereby allowing a practitioner to easily dispense a specific amount of two different components of a dental composition in precise ratios to one another with the use of only one hand.

Turning now to FIGS. 5a, 5b, 5c, and 5d, cartridge 30 preferably engages cartridge retaining spring 28 to help seat cartridge 30 into cartridge retaining slot 12a. Cartridge retaining spring 28 resists upward movement of cartridge 30 inside of chamber 13 as cartridge 30 rests in the cartridge retaining slot 12a. However as shown generally in FIG. 7, when cartridge ejector button 50 is depressed, ejector 45 is advanced, causing cartridge 30 to become unseated from cartridge retaining slot 12a and allowing cartridge ejector spring 46 to propel cartridge 30 from chamber 13. (See, for example, FIG. 7) Further, as the ramp 47 on ejector 45 elevates cartridge 30, drive spring 25 and pawl spring 26 are elevated to allow rack system 21 to be urged out of the lumens 32 of cartridge 30 and fully pulled to its starting position by rack return springs 27. Optionally, cartridge 30 may be shaped to include a notch (not shown) in its rear portion for interfacing with a corresponding protruding portion in chamber 13 to prevent cartridge from being inadvertently removed when cap 60 is removed from chamber. Further, according to one embodiment, it will be appreciated that an ejector button return spring 55 (see FIGS. 4 and 4a) is optionally used to return the ejector 45 and ejector button 50 (see FIG. 3c) to its original position after it is depressed.

According to yet another embodiment shown in FIG. 7, ejector 45 optionally comprises a ramp 47, a drive spring disengaging portion 48, and a pawl spring disengaging portion 49, all of which act in combination to eject cartridge 30 from chamber 13 while allowing rack springs 27 to fully disengage pistons 31, and return to its fully extended position to clear the lumens of cartridge 30. Therefore, when ejector button 50 (see FIG. 3) is pressed in a direction toward chamber 13, ejector 45 is urged toward chamber 13, thereby causing ramp 47 to disengage the cartridge 30 from its seated position in lower shell 12 by lifting engaging portion 33 of cartridge 30 to elevate cartridge 30 from retaining slot 12a of bottom shell 12 such that cartridge ejector spring 46 urges cartridge 30 away from slot 12a and out of chamber 13. Simultaneously, as ejector button 50 was urged toward chamber 13, drive spring disengaging portion 48 and pawl spring disengaging portion 49 are lifted away from teeth 23 of rack system 21 such that rack return springs 27 allow rack system 21 to return to its fully retracted position away from chamber 13.

Yet another aspect of one embodiment of the present application relates to a design of replaceable cartridge 30. According to one embodiment, cartridge 30 comprises at least two lumens 32. It will be appreciated that multiple lumens, including 3 or more lumens 32 may be employed, as required in view of the number of components that should be stored separately and dispensed together to achieve the desired dental composition. According to the exemplary embodiment, cartridge 30 comprises two lumens comprising a translucent, transparent, or opaque polymer, such as polyethylene, acrylic, or polycarbonate polymer. It will be appreciated that the selection of the polymer or other material (such as glass, hard plastics, etc.) that is used to construct the lumens, can vary with regard to its chemical compatibility with components of the dental composition 38 contained in the lumen, depending upon the dental compositions intended for use therein. The lumens may contain, for example, various components of multi-component dental adhesive systems, colorant systems, cement systems, or other dental restorative systems, such as the components included in ALLBOND 2®, DUOLINK®, RESINOMER®, and TYRIAN® (available from Bisco, Inc., Schaumburg, Ill.) systems, or may include any flowable multiple component dental compound, it being appreciated that adjustments may be required to achieve the required viscosity of the component for ease of dispensing from the dispenser. It will also be appreciated that the components of two component or multiple component dental systems that, upon admixing of the components, initiate curing or hardening, may be disposed in separate lumens 32 of cartridges 30 for metered dispensing admixing according to the present invention. Additionally, dental compositions that change colors upon admixing and/or subsequent curing or hardening can be employed in the separate lumens 32 and dispensed therefrom according to the present invention. It is well known that some dental compositions cure in the presence of certain radiation, and some components of a dental compositions may be sensitive to radiation in the wavelengths from 380 to 520 nm or other wavelengths of light operable to cure or degrade the particular dental composition, and therefore a translucent or opaque cartridge or lumen that is operable to block radiation, such as light, in those wavelengths would be preferable. In addition, use of a transparent material for chamber 13 in combination with a transparent or translucent polymer or other material for cartridge 30 allows a practitioner or lab technician to monitor the amount of dental composition left in the lumens of cartridge 30 so that the cartridge may be replaced at the appropriate time.

Although several embodiments have been described in considerable detail above and in the accompanying figures and appendices herein, such description is offered as non-limiting examples of the present invention as many other versions of the present invention are possible. It is anticipated that a variety of modifications and changes will be apparent to those having ordinary skill in the art and that such modifications and changes are intended to be encompassed within the spirit and scope of the present invention as defined by any later appended claims. Further, additional embodiments of the present invention are anticipated.

What is claimed is:

1. An apparatus for dispensing dental compositions, the apparatus comprising:
   a) a body comprising a top shell portion, a bottom shell portion, and a chamber received therein;
   b) a replaceable cartridge having at least two lumens with at least two pistons, the cartridge operable to dispense a component of a dental compound contained within the lumens, and wherein the cartridge is further operable to be at least partially inserted into the chamber;
   c) an inner mechanical system disposed in the body, the inner mechanical system comprising a rack system, said rack system having at least two racks operable to be urged forward to engage a piston in each lumen of the cartridge;
   d) a button system in contact with the body, the button system operable to be depressed in a direction substantially forward and in line with the rack system by a user such that the button system engages the inner mechanical system when depressed, such that the rack is advanced a predetermined distance such that a metered amount of the components of the dental compound is dispensed from the at least two lumens; and
   e) wherein the inner mechanical system further comprises a plurality of teeth disposed on the rack system, and a drive spring and a pawl spring disposed on the body, the drive spring and the pawl spring being operable to interface with at least one of a plurality of teeth on the rack system and at least one surface of the button system such that depression of the button system by a user initiates drive spring to advance the rack system a predetermined distance proportional to the distance between a first selected tooth located on the rack and a second selected tooth located on the rack and initiates the pawl spring to disengage from a third selected tooth on the rack and engage a fourth selected tooth on the rack located at a distance substantially equal to the distance between the first tooth and the second tooth, and release of the button causes the drive spring to disengage from said first selected tooth and engage the second selected tooth on the rack.

2. The apparatus of claim 1, wherein a cross section area of a first lumen of the at least two lumens when compared to a cross section area of a second lumen of the at least two lumens is proportionally sized to equal the desired volumetric ratio of a first component of the dental compound in a first lumen to the volumetric ratio of a second component of the dental compound in a second lumen.

3. The apparatus of claim 2, wherein the ratio of the cross section area of the first lumen of the at least two lumens is approximately 1 to 4 times the cross section area of the second lumen of the at least two lumens.

4. The apparatus of claim 2, wherein the ratio of cross section area of the first lumen of the at least two lumens to the cross section area of the second lumen of the at least two lumens is approximately 1:1.

5. The apparatus of claim 2, wherein the ratio of cross section area of the first lumen of the at least two lumens to the cross section area of the second lumen of the at least two lumens is approximately 2:1.

6. The apparatus of claim 2, wherein the ratio of cross section area of the first lumen of the at least two lumens to the cross section area of the second lumen of the at least two lumens is approximately 3:1.

7. The apparatus of claim 2, wherein the ratio of cross section area of the first lumen of the at least two lumens to the cross section area of the second lumen of the at least two lumens is approximately 4:1.

8. The apparatus of claim 2, wherein the metered amount of the dental compound is between about 0.04 ml and about 0.20 ml for each depression of the button system.

9. The apparatus of claim 1, wherein the rack system comprises at least two racks positioned in parallel with one another and a plurality of teeth disposed on each rack, and the inner mechanical system comprises a drive spring operable to engage teeth on each rack and the button system, the racks each containing a plurality of teeth on each rack corresponding with one another and operable to be engaged and moved a predetermined distance by the drive spring when the button system is depressed by a user.

10. The apparatus of claim 1, wherein the replaceable cartridge further comprises a chamber engaging portion operable to fit within a retaining slot located within the body chamber when the cartridge is seated into the body chamber.

11. The apparatus of claim 10, further comprising a cartridge ejector system attached to the body, operable to disengage the cartridge from the body chamber when the ejector system is engaged.

12. The apparatus of claim 1, further comprising an anti-hysteresis system in engagement with the rack system, the anti-hysteresis system operable to prevent the rack system from moving backward unless the anti-hysteresis system is disengaged.

13. An apparatus for dispensing dental compositions, the apparatus comprising:
a) a body comprising a top shell portion, a bottom shell portion, and a chamber received therein;
b) a cartridge operably attached to the body, the cartridge having at least two lumens with at least two pistons, the cartridge operable to dispense a component of a dental compound contained within the lumens;
c) an inner mechanical system disposed in the body, the inner mechanical system comprising a rack system, said rack system having at least two racks operable to be urged forward to engage a piston in each lumen of the cartridge, the inner mechanical system further comprising a drive spring and a pawl spring operable to interface with at least one of a plurality of teeth on the rack system;
d) a button system in contact with the body and in proximity to the drive spring, the button system operable to be depressed by a user in a substantially forward direction such that at least one surface of the button system engages the drive spring when a user depresses the button system such that depression of the button initiates the drive spring to advance the rack system a predetermined distance proportional to the distance between a first selected tooth located on the rack and a second selected tooth located on the rack, initiating the pawl spring to disengage from a third selected tooth on the rack and to engage a fourth selected tooth on the rack located at a distance substantially equal to the distance between the first tooth and the second tooth, and whereby release of the button system by the user causes the drive spring to disengage from said first tooth and engage the second tooth on the rack, causing the rack to advance a predetermined distance such that a metered amount of the components of the dental compound is dispensed from both lumens.

14. The system of claim 13, wherein the cartridge comprises a translucent material operable to preclude radiation of a selected range of wavelengths from reaching the dental composition contained in one or both lumens of the cartridge.

15. The system of claim 13, further comprising an ejector system in contact with the body, and adjacent to the cartridge, the ejector system operable to disengage the cartridge from the dispensing apparatus when an ejector button is activated.

16. The system of claim 15, wherein the proportion of each component of the dental composition is determined by the cross section area of the lumen containing the component.

17. The system of claim 15, wherein the inner mechanical system further comprises a pawl spring in contact with at least one of the teeth on each rack, the pawl spring operable to prevent the rack system from moving in a direction opposite of the pistons when the pawl spring is engaged.

18. The system of claim 15, wherein the ejector is further operable to disengage the drive spring and the pawl spring when the ejector button is activated.

19. The system of claim 18, wherein the dental composition comprises a first and second component.

20. The system of claim 19, wherein the ratio of the cross section area of the first lumen is approximately 1 to 4 times the cross section area of the second lumen.

21. The system of claim 19, wherein the ratio of cross section area of the first lumen to the cross section area of the second lumen is approximately 1:1.

22. The system of claim 19, wherein the ratio of cross section area of the first lumen to the cross section area of the second lumen is approximately 2:1.

23. The system of claim 19, wherein the ratio of cross section area of the first lumen to the cross section area of the second lumen is approximately 3:1.

24. The system of claim 19, wherein the ratio of cross section area of the first lumen to the cross section area of the second lumen is approximately 4:1.

* * * * *